United States Patent
Kokubo et al.

(10) Patent No.: US 8,470,387 B2
(45) Date of Patent: Jun. 25, 2013

(54) BONE REPAIR MATERIAL AND METHOD FOR PRODUCING THE SAME

(75) Inventors: Tadashi Kokubo, Kasugai (JP); Takashi Kizuki, Kasugai (JP); Seiji Yamaguchi, Kasugai (JP); Tomiharu Matsushita, Kasugai (JP)

(73) Assignee: Advanced Medix Inc., Nagaokakyo-shi, Kyoto (JP)

( * ) Notice: Subject to any disclaimer, the term of this patent is extended or adjusted under 35 U.S.C. 154(b) by 167 days.

(21) Appl. No.: 12/995,850

(22) PCT Filed: Jun. 1, 2009

(86) PCT No.: PCT/JP2009/002426
§ 371 (c)(1),
(2), (4) Date: Dec. 2, 2010

(87) PCT Pub. No.: WO2009/147819
PCT Pub. Date: Dec. 10, 2009

(65) Prior Publication Data
US 2011/0082562 A1    Apr. 7, 2011

(30) Foreign Application Priority Data

Jun. 3, 2008  (JP) .................... 2008-145794

(51) Int. Cl.
*A61K 6/033* (2006.01)
*B05D 3/02* (2006.01)
*B05D 3/04* (2006.01)

(52) U.S. Cl.
USPC ..... 427/2.26; 427/2.24; 427/2.27; 427/372.2; 427/377

(58) Field of Classification Search
USPC ............... 427/2.1, 2.24, 2.26, 2.27, 372.2
See application file for complete search history.

(56) References Cited

U.S. PATENT DOCUMENTS 5,871,595 A * 2/1999 Ahmed et al. ............ 148/421

FOREIGN PATENT DOCUMENTS

| JP | 8-299429 A | 11/1996 |
|----|-----------|---------|
| JP | 10-179717 A | 7/1998 |
| JP | 10-179718 A | 7/1998 |
| JP | 10179717 A * | 7/1998 |
| JP | 2000-093498 A | 4/2000 |
| JP | 2000-102601 A | 4/2000 |

(Continued)

OTHER PUBLICATIONS

Uchida et al. Effect of Water Treatment on the Apatite-Forming Ability of NaOH-Treated Titanium Metal. Journal of Biomedical Materials Research, vol. 63, Issue 5, 2002 pp. 522-530.*

(Continued)

*Primary Examiner* — Timothy Meeks
*Assistant Examiner* — Cachet Sellman
(74) *Attorney, Agent, or Firm* — Westerman, Hattori, Daniels & Adrian, LLP

(57) ABSTRACT

A bone repair material being superior in apatite-forming ability and its stability in a storage and high in scratch resistance is disclosed. The material is produced by a method comprising the steps of: immersing a substrate made of titanium or a titanium alloy in a first aqueous solution that does not contain calcium ions but contains at least one cation selected from the group consisting of sodium ions and potassium ions and is alkaline; immersing the substrate in a second aqueous solution that does not contain phosphate ions but contains calcium ions; heating the substrate in a dry atmosphere; and treating the substrate with hot water of 60° C. or higher or with steam.

8 Claims, 4 Drawing Sheets

FOREIGN PATENT DOCUMENTS

| JP | 2002-345948 A | 12/2002 |
|---|---|---|
| JP | 2004-183017 A | 7/2004 |
| JP | 2006-102212 A | 4/2006 |

OTHER PUBLICATIONS

Kokubo et al. JP10179717A Translation 1998.*

Nishimura, J. et al. "Effect of alkali-release treatment on apatite-forming ability of alkali-treated titanium metal," 13th Fall Meeting of The Ceramic Society of Japan, Oct. 11, 2000, vol. 13, pp. 86, 1J09.

Fujibayashi, Sunsuke "Bioactive Titanium: Effect of sodium removal treatment on bone bonding ability of bioactive titanium prepared by alkali and heat treatment," Japanese Society for Biomaterials Symposium Yokoshu, Nov. 1, 2000, vol. 2000, pp. 36, A2-4.

Fujibayashi, Shunsuke et al. "Seitai Kassel Titanium—Natrium Jokyo Shori ga Alkali Kanetsu Shori Titanium no Hone Ketsugono ni Oyobosu Eikyo-," The Journal of the Japanese Orthopaedic Association, Aug. 25, 2001, vol. 75 No. 8, pp. S1140.

Kaneko, H. et al. "Mechanism of apatite formation on titanium metal subjected to NaOH and hot-water treatments," 14th Fall Meeting of the Ceramic Society of Japan celebrating 21st Century, Sep. 26-28, 2001, pp. 264.

Armitage, D.A. et al. "The oxidation of calcium implanted titanium in water: A depth profiling study," Applied Surface Science, Available online Oct. 17, 2006, vol. 253, pp. 4085-4093.

Kim, Hyun-Min et al. "Preparation of bioactive Ti and its alloys via simple chemical surface treatment," Journal of Biomedical Materials Research, Feb. 1996, vol. 32, pp. 409-417.

Nakagawa, M. et al. "Effects of hydrothermal treatment with CaCl2 solution on surface property and cell response of titanium implants," Journal of Materials Science: Materials in Medicine, May 2005, vol. 16, pp. 985-991.

Park, Jin-Woo et al. "Effects of calcium ion incorporation on bone healing of Ti6A14V alloy implants in rabbit tibiae," Biomaterials, Available online Apr. 10, 2007, vol. 28, pp. 3306-3313.

Wang, Xiao-Xiang et al. "Bioactive titania gel layers formed by chemical treatment of Ti substrate with a H2O2/HC1 solution," Biomaterials, Accepted Jul. 11, 2001, vol. 23, pp. 1353-1357.

International Search Report of PCT/JP2009/002426, mailing date Jul. 7, 2009.

* cited by examiner

Before moisture-resistance test

After moisture-resistance test

BONE REPAIR MATERIAL AND METHOD FOR PRODUCING THE SAME

TECHNICAL FIELD

The present invention relates to bone repair materials and methods for producing the same. These bone repair material can be used suitably for bone repair at a portion to which a large load is applied, such as the femur, the hip joint, the vertebra, and the tooth root.

BACKGROUND ART

Titanium or alloys thereof on the surface of which an apatite layer is formed are expected as a bone repair material to be used at a portion to which a large load is applied because it has a high fracture toughness and can bond to living bone via apatite in living body. Accordingly, various methods for forming an apatite layer on the surface of a substrate made of titanium or alloys thereof have been investigated. Among these, a product obtained by immersing an alkali-treated substrate in an aqueous solution supersaturated with respect to apatite to deposit apatite is prone to produce cracking in apatite at the time of drying. Moreover, as to a product obtained by plasma-spraying apatite to a substrate, apatite is prone to crack at the time of cooling due to the difference in thermal expansion between apatite and the substrate. For this reason, there have been proposed various methods for producing a bone repair material of titanium or alloys thereof on the surface of which a titanate layer having an apatite-forming ability is formed in order to form apatite in the body and, at the same time, bond it to living bone (Patent Documents 1 to 8, Non-Patent Documents 1 to 5).

[Patent Document 1] WO 95/13100
[Patent Document 2] JP 08-299429 A
[Patent Document 3] JP 2004-183017 A
[Patent Document 4] JP 10-179717 A
[Patent Document 5] JP 10-179718 A
[Patent Document 6] JP 2000-93498 A
[Patent Document 7] JP 2006-102212 A
[Patent Document 8] JP 2000-102601 A
[Non-Patent Document 1] Kim, et al., J. Biomed. Mater. Res., Vol. 32, p. 409-417 (1996)
[Non-Patent Document 2] Nakagawa, et al., J. Mat. Sci: Mat. Med., Vol. 16, p. 985-991 (2005)
[Non-Patent Document 3] Wang, et al., Biomaterials, Vol. 23, p. 1353-1357 (2002)
[Non-Patent Document 4] Park, et al., Biomaterials, Vol. 28, p. 3306-3313 (2007)
[Non-Patent Document 5] Armitage, et al., Appl. Surf. Sci., Vol. 253, p. 4085-4093 (2007)

DISCLOSURE OF THE INVENTION

Problems to be Solved by the Invention

However, materials obtained by the methods disclosed in Patent Document 1 and Non-Patent Document 1 lose their apatite-forming ability if they are exposed to a high-humidity condition at a high-temperature for a long time as an accelerated test simulating long term storage. Therefore, inventories cannot be stocked until repair surgeries. On the other hand, materials obtained by the methods disclosed in Patent Documents 2 to 4, 6, and 7 and Non-Patent Documents 2 and 3 are so low in scratch resistance that their titanate layers are prone to peel off during the surgery for implanting the material into the body. Materials obtained by the method disclosed in Patent Documents 5 and 8 and Non-Patent Document 5 are so poor in apatite-forming ability that they require 10 days for forming apatite on a whole surface. If such a long time is required in a living body, organic components will adhere to their surfaces before apatite is formed and, as a result, they will become incapable of bonding to living bone. A material obtained by the method disclosed in Patent Document 6 also is low in scratch resistance and will deteriorate with respect to its apatite-forming ability if it is heated. The method disclosed in Non-Patent Document 4 requires a high temperature and a high pressure, resulting in a remarkable high cost.

Therefore, an object of the present invention is to provide a bone repair material that is superior in apatite-forming ability and its stability in a storage and is high in scratch resistance.

Means for Solving the Problems

According to one aspect of the present invention, a bone repair material includes a substrate made of titanium or a titanium alloy, and a titanate layer that has been formed on the substrate and contains calcium whose concentration decreases with increasing depth from a surface of the layer, wherein the titanate layer exhibits a scratch resistance of 20 mN or more when vibration 100 μm in amplitude is added to a stylus with a spring constant of 200 g/mm and the stylus is moved at a rate of 10 mm/sec under the application of a load increasing at a rate of 100 mN/min, and the bone repair material has an ability that apatite is formed on the whole surface of the material within 3 days in a living body or in a simulated body fluid.

According to this bone repair material, the calcium concentration in the titanate layer decreases with increasing depth. Therefore, the titanium concentration conversely increases with increasing depth, so that the titanate layer bonds strongly to the substrate and, as a result, the aforementioned high scratch resistance is exhibited. Moreover, the material has a superior apatite-forming ability because calcium is enriched and activated at a portion that is close to the surface.

An appropriate method for producing the bone repair material of the present invention is characterized by including the steps of immersing a substrate made of titanium or a titanium alloy in a first aqueous solution that does not contain calcium ions but contains one or more kinds of cations of sodium ions and potassium ions and is alkaline, immersing the substrate in a second aqueous solution that does not contain phosphate ions but contains calcium ions, heating the substrate in a dry atmosphere, and treating the substrate with hot water of 60° C. or higher or with steam.

By the immersion in the first aqueous solution, the substrate and the aqueous solution react with each other, so that a layer of sodium hydrogen titanate or potassium hydrogen titanate is formed easily on a surface of the substrate. This surface layer is known to have such a gradient structure that the sodium concentration or the potassium concentration decreases with increasing depth from its surface (Kim et al., J. Biomed. Mater. Res., Vol. 45, p. 100-109, (1999)). If the substrate is then immersed in the second aqueous solution, sodium ions or potassium ions located in the surface layer are exchanged for calcium ions in the aqueous solution. Such stepwise immersion of a substrate in two different aqueous solutions forms the aforementioned titanate layer with a gradient composition containing calcium in a high concentration on the substrate. This layer is dehydrated to turn into a mechanically and chemically stable anhydrous titanate layer when being heated in a dry atmosphere, so that the scratch resistance is improved greatly. A subsequent treatment with hot water or steam of 60° C. or higher activates the surface to a degree such that the surface can demonstrate a prescribed apatite-forming ability. The apatite-forming ability is so high that it will take only 3 days to form apatite on the whole surface, and is maintained even after a long term storage.

Effect of the Invention

As described above, a bone repair material obtained by the production method of the present invention is superior in apatite-forming ability and has high scratch resistance and, therefore, it can bond to living bone rapidly to repair a bone defect when it is implanted at a portion in a living body to which a large load is applied. Moreover, inventories can be used for surgeries because of the superior stability in a storage of the bone repair material.

BEST MODE FOR CARRYING OUT THE INVENTION

Figure 1:
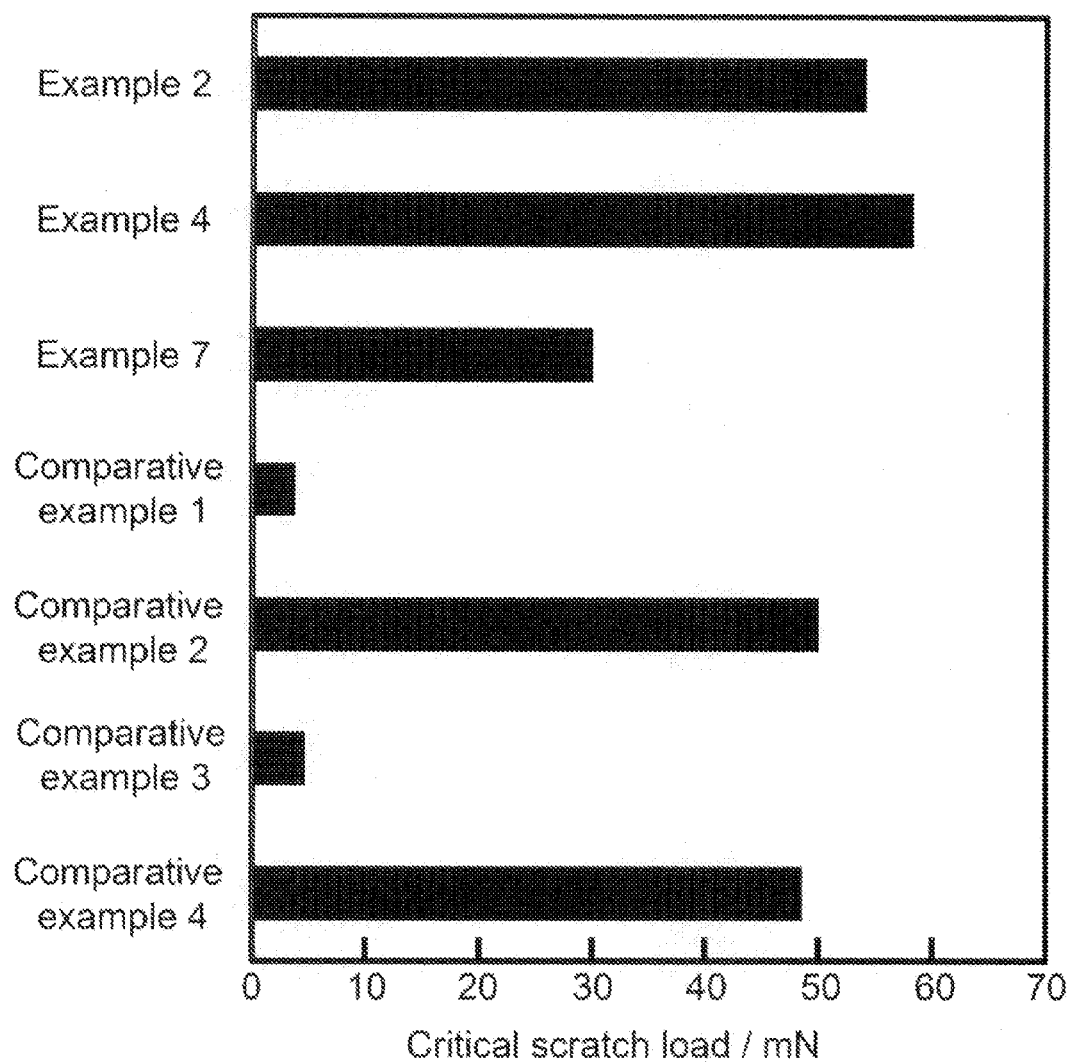
FIG. 1 is a graph showing the scratch load of surfaces of the specimens of examples and comparative examples.

It is preferable that the titanate layer have a calcium concentration of from 0.1 to 20 atom % within a region to a depth of at least 1 μm from the surface. When the calcium concentration is less than 0.1 atom %, too small amount of the calcium component which will nucleate apatite is present on the surface, so that apatite is hardly formed. If it exceeds 20 atom %, since the surface layer will become a too stable compound, apatite is hardly formed.

It is preferable that the titanate layer has a thickness of from 0.1 to 10 μm. When the thickness is less than 0.1 μm, too small amount of the calcium component which will nucleate apatite is present on the surface, so that apatite is hardly formed. If it exceeds 10 μm, the titanate layer will become prone to be peeled off from the substrate.

A preferred alkali concentration of the first aqueous solution is from 0.1 to 20 M and a preferred calcium ion concentration of the second aqueous solution is from 0.1 to 1,000 mM. In either case, a preferred immersion temperature and a preferred immersion time are from 5 to 99° C. and from 0.5 to 48 hours, respectively. This is because if either one item is less than the lower limit thereof, a titanate layer with the aforementioned preferable thickness or preferable gradient composition is hardly formed, whereas if either one item exceeds the upper limit thereof, the titanate layer becomes so thick that it becomes prone to be peeled off from the substrate.

The second aqueous solution is prepared preferably by dissolving one or more kinds of salts selected from calcium chloride, calcium nitrate, calcium acetate, and calcium hydroxide in water.

The heating temperature after the aqueous solution treatment is preferably from 400 to 800° C. When the temperature is lower than 400° C., both the mechanical strength and the chemical stability of a titanate layer are hardly improved.

A preferred temperature of the hot water treatment or the steam treatment is from 60 to 99° C. or from 100 to 180° C., respectively, and a preferred treatment time is from 0.1 to 48 hours.

EXAMPLES

Production Conditions

Example 1

A pure titanium metal plate having a size of 10 mm×10 mm×1 mm was polished with a #400 diamond pad, ultrasonically washed with acetone, 2-propanol and ultrapure water each for 30 minutes, and then immersed in 5 ml of a 5 M aqueous sodium hydroxide solution at 60° C. for 24 hours (hereinafter, referred to as an "alkali treatment"), and washed with ultrapure water for 30 seconds. This titanium metal plate was immersed in 10 ml of a 100 mM aqueous calcium chloride solution at 40° C. for 24 hours (hereinafter, referred to as a "calcium treatment") and was washed with ultrapure water for 30 seconds. Subsequently, the titanium metal plate was heated from room temperature to 600° C. at a rate of 5° C./min in an electric furnace, held at 600° C. for one hour, and then allowed to cool in the furnace (hereinafter, referred to as a "heat treatment"). Then, a specimen was produced by immersing the titanium metal plate in 10 ml of ultrapure water at 60° C. for 24 hours (hereinafter, referred to as a "hot water treatment") and subsequently washing the plate with ultrapure water for 30 seconds.

Example 2

A specimen was produced under the same conditions as those used in Example 1 except for adjusting the temperature of ultrapure water to be used in the hot water treatment to 80° C.

Example 3

A specimen was produced under the same conditions as those used in Example 1 except for adjusting the temperature of ultrapure water to be used in the hot water treatment to 95° C.

Example 4

A specimen was produced under the same conditions as those used in Example 1 except for treating a titanium metal plate with steam of 121° C. in an autoclave for 20 minutes instead of doing the hot water treatment.

Example 5

A specimen was produced under the same conditions as those used in Example 1 except for using an aqueous calcium nitrate solution instead of the aqueous calcium chloride solution and adjusting the temperature of ultrapure water to be used in the hot water treatment to 80° C.

Example 6

A specimen was produced under the same conditions as those used in Example 1 except for using an aqueous calcium acetate solution instead of the aqueous calcium chloride solution and adjusting the temperature of ultrapure water to be used in the hot water treatment to 80° C.

Example 7

A specimen was produced under the same conditions as those used in Example 1 except for adjusting the holding temperature of the electric furnace to 800° C. and adjusting the temperature of ultrapure water to be used in the hot water treatment to 80° C.

Example 8

A specimen was produced under the same conditions as those used in Example 1 except for using a Ti-6Al-4V alloy plate instead of the pure titanium metal plate and adjusting the temperature of ultrapure water to be used in the hot water treatment to 80° C.

Example 9

A specimen was produced under the same conditions as those used in Example 1 except for using a Ti-15Mo-5Zr-3Al alloy plate instead of the pure titanium metal plate and adjusting the temperature of ultrapure water to be used in the hot water treatment to 80° C.

Example 10

A specimen was produced under the same conditions as those used in Example 1 except for using a Ti-6Al-2Nb-1Ta alloy plate instead of the pure titanium metal plate and adjusting the temperature of ultrapure water to be used in the hot water treatment to 80° C.

Example 11

A specimen was produced under the same conditions as those used in Example 1 except for using a Ti-15Zr-4Nb-4Ta alloy plate instead of the pure titanium metal plate and adjusting the temperature of ultrapure water to be used in the hot water treatment to 80° C.

Example 12

A specimen was produced under the same conditions as those used in Example 1 except for using a Ti-29Nb-13Ta-4.6Zr alloy plate instead of the pure titanium metal plate, using a 1 M aqueous sodium hydroxide solution instead of the 5 M aqueous sodium hydroxide solution, adjusting the holding temperature of the electric furnace to 700° C. instead of 600° C., and adjusting the temperature of ultrapure water to be used in the hot water treatment to 80° C. instead of 60° C.

Example 13

A specimen was produced under the same conditions as those used in Example 1 except for using a Ti-36Nb-2Ta-3Zr-0.30 alloy plate instead of the pure titanium metal plate, using a 1 M aqueous sodium hydroxide solution instead of the 5 M aqueous sodium hydroxide solution, adjusting the holding temperature of the electric furnace to 700° C. instead of 600° C., and adjusting the temperature of ultrapure water to be used in the hot water treatment to 80° C. instead of 60° C.

Comparative Example 1

A specimen was produced by polishing a pure titanium metal plate having a size of 10 mm×10 mm×1 mm with a #400 diamond pad, ultrasonically washing the plate with acetone, 2-propanol, and ultrapure water each for 30 minutes, then performing an alkali treatment under the same conditions as those used in Example 1, and then washing the plate with ultrapure water for 30 seconds.

Comparative Example 2

A comparative substrate obtained under the same conditions as those used in Comparative Example 1 was heat-treated under the same conditions as those used in Example 1.

Comparative Example 3

A comparative substrate obtained under the same conditions as those used in Comparative Example 1 was calcium-treated under the same conditions as those used in Example 1.

Comparative Example 4

A comparative substrate obtained under the same conditions as those used in Comparative Example 1 was calcium-treated and further heat-treated under the same conditions as those used in Example 1.

Comparative Example 5

A comparative substrate obtained under the same conditions as those used in Comparative Example 1 was heat-treated under the same conditions as those used in Example 1 and then was calcium-treated under the same conditions as those used in Example 1.

[Evaluation of Apatite-Forming Ability]

The specimens of the examples and the comparative examples were immersed in a simulated body fluid (SBF) of ISO 23317 kept at 36.5° C. and, as a result, apatite was formed within 72 hours from the commencement of the immersion in the simulated body fluid for all the specimens except for Comparative Example 4 as shown in Table 1. In addition, as to the specimens of all the examples and Comparative Example 2, apatite was formed on the whole surface of each specimen. In sum, it was demonstrated that these specimens had a high apatite-forming ability in a living body.

TABLE 1

| sample | substrate | treatment | apatite-forming ability*[1] |
|---|---|---|---|
| Example 1 | Ti metal | NaOH—CaCl$_2$-heat600° C.-water60° C. | +++ |
| Example 2 | Ti metal | NaOH—CaCl$_2$-heat600° C.-water80° C. | +++ |
| Example 3 | Ti metal | NaOH—CaCl$_2$-heat600° C.-water95° C. | +++ |
| Example 4 | Ti metal | NaOH—CaCl$_2$-heat600° C.-autoclave | +++ |

TABLE 1-continued

| sample | substrate | treatment | apatite-forming ability*[1] |
|---|---|---|---|
| Example 5 | Ti metal | NaOH—Ca(NO$_3$)$_2$-heat600° C.-water80° C. | +++ |
| Example 6 | Ti metal | NaOH—Ca(CH$_3$COO)$_2$-heat600° C.-water80° C. | +++ |
| Example 7 | Ti metal | NaOH—CaCl$_2$-heat800° C.-water80° C. | +++ |
| Example 8 | Ti—6Al—4V alloy | NaOH—CaCl$_2$-heat600° C.-water80° C. | +++ |
| Example 9 | Ti—15Mo—5Zr—3Al alloy | NaOH—CaCl$_2$-heat600° C.-water80° C. | +++ |
| Example 10 | Ti—6Al—2Nb—1Ta alloy | NaOH—CaCl$_2$-heat600° C.-water80° C. | +++ |
| Example 11 | Ti—15Zr—4Nb—4Za alloy | NaOH—CaCl$_2$-heat600° C.-water80° C. | +++ |
| Example 12 | Ti—29Nb—13Ta—4.6Zr alloy | NaOH—CaCl$_2$-heat700° C.-water80° C. | +++ |
| Example 13 | Ti—36Nb—2Ta—3Zr—0.3O alloy | NaOH—CaCl$_2$-heat700° C.-water80° C. | +++ |
| Comparative example 1 | Ti metal | NaOH | + |
| Comparative example 2 | Ti metal | NaOH-heat600° C. | +++ |
| Comparative example 3 | Ti metal | NaOH—CaCl$_2$ | ++ |
| Comparative example 4 | Ti metal | NaOH—CaCl$_2$-heat600° C. | − |
| Comparative example 5 | Ti metal | NaOH-heat600° C.-CaCl$_2$ | + |

*[1]Rate of apatite-covered area −: 0%, +: 10~50%, ++: 50~90%, +++: 100%

[Measurement of Scratch Resistance]

Using a scratch testing machine CSR-2000 manufactured by Rhesca Corporation, vibration 100 μm in amplitude was added to a stylus with a spring constant of 200 g/mm on a specimen, and the stylus was moved at a rate of 10 mm/sec under a load increasing at a rate of 100 mN/min. A critical scratch load at this time was measured. As a result, as shown in FIG. 1, the load was 5 mN or less before a heat treatment (Comparative Example 1, Comparative Example 3), but it increased drastically to about 50 mN after a heat treatment at 600° C. (Comparative Example 2, Comparative Example 4). Moreover, the load did not decrease even when a hot water treatment or a steam treatment was performed (Example 2, Example 4). On the other hand, when a heat treatment at 800° C. was performed (Example 7), the scratch load of a surface layer decreased to about half of that measured when a heat treatment was performed at 600° C.

[Evaluation of Stability in Storage]

Figure 2:
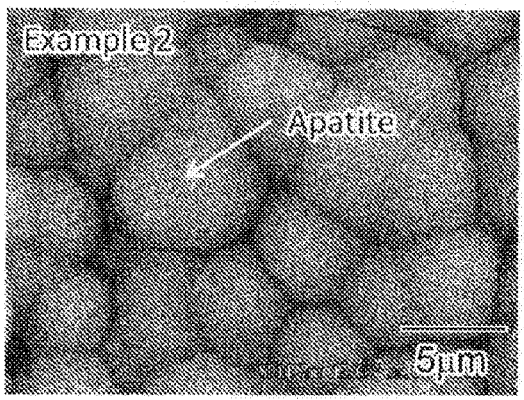
FIG. 2 includes SEM images of the surfaces of specimens taken 72 hours after the immersion in a simulated body fluid executed before or after a moisture resistance test.
Figure 2:
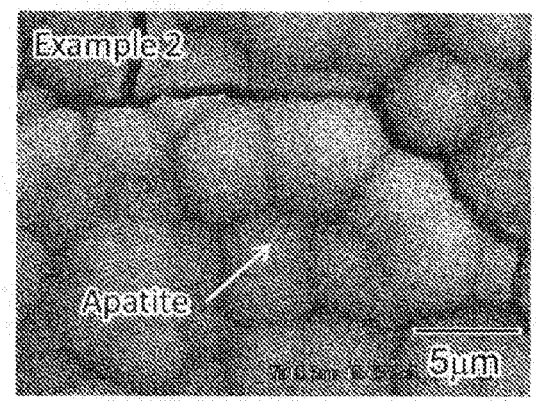
Figure 2:
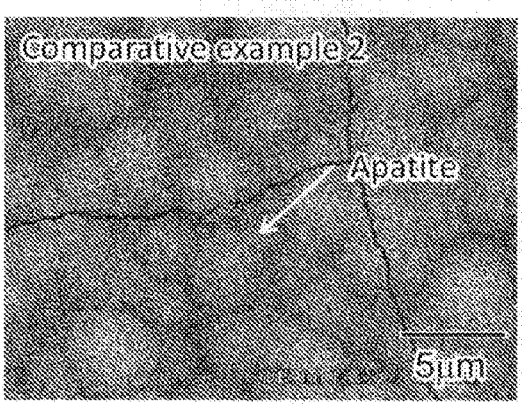
Figure 2:
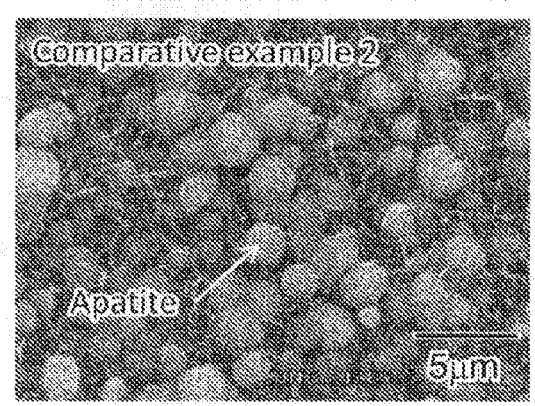

The specimens of Example 2 and Comparative Example 2 were subjected to a moisture resistance test that includes exposing the specimens to an atmosphere characterized by a relative humidity of 95% at a temperature of 80° C. for one week and then were immersed in a simulated body fluid. As a result, as shown in FIG. 2, the specimen of Example 2 was covered on its whole surface with apatite within 72 hours of the immersion in the simulated body fluid as before the moisture resistance test. In sum, it was demonstrated that the specimen did not lose its high apatite-forming ability even when it was placed under high-humidity condition at a high-temperature for a long time. Conversely, it was found that the specimen of Comparative Example 2 formed apatite only on part of the surface of the specimen and the apatite-forming ability deteriorated remarkably under a high-humidity condition at a high-temperature.

[Compositional Analysis]

When the composition of the surface of each specimen was analyzed by the energy dispersive X-ray analysis at an accelerating voltage of 9 kV, 5.2 atom % of sodium was detected in an alkali-treated specimen (Comparative Example 1) as shown in Table 2. As to a specimen that was further subjected to a calcium treatment (Comparative Example 3), sodium disappeared and about 4 atom % of calcium was newly detected instead. Even when these were further subjected to a heat treatment (Comparative Example 4) or a hot water treatment (Example 2), there was little change in these values.

TABLE 2

| | element/atom % | | | | |
|---|---|---|---|---|---|
| sample | Ti | O | C | Na | Ca |
| Example 2 | 24.8 | 64.9 | 6.8 | 0.0 | 3.5 |
| Example 4 | 26.4 | 64.3 | 6.8 | 0.0 | 2.6 |
| Example 5 | 24.3 | 65.4 | 6.4 | 0.0 | 3.9 |
| Example 6 | 26.0 | 69.2 | 1.8 | 0.0 | 3.1 |
| Example 7 | 25.6 | 65.4 | 5.0 | 0.0 | 4.1 |
| Comparative example 1 | 26.9 | 63.1 | 4.8 | 5.2 | — |
| Comparative example 2 | 26.3 | 65.1 | 3.0 | 5.5 | — |
| Comparative example 3 | 26.2 | 63.8 | 6.1 | 0.0 | 3.9 |
| Comparative example 4 | 25.6 | 63.8 | 6.7 | 0.0 | 3.8 |
| Comparative example 5 | 27.4 | 66.0 | 3.5 | 1.9 | 0.6 |

Figure 3:
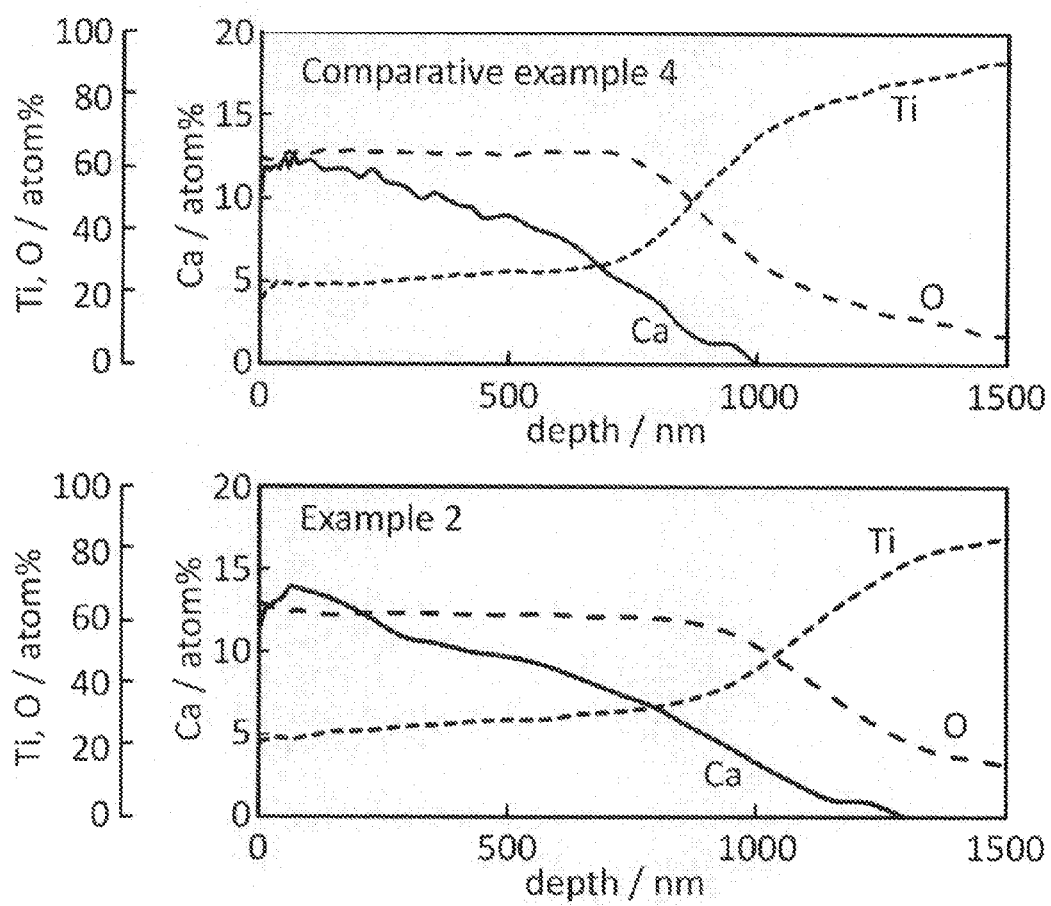
FIG. 3 includes graphs each showing the result of Auger spectroscopy analysis representing the ion distribution near the surface of titanium metal having been subjected to a calcium treatment.

According to Auger spectroscopy, it was shown that when a calcium treatment was conducted on a substrate after an alkali treatment and then a heat treatment was conducted (Comparative Example 4), calcium ions entered to a depth of 1 μm from the surface and the concentration thereof decreased gradually with depth as shown in FIG. 3. Even when this substrate was further subjected to a hot water treatment (Example 2), no major change was observed in the gradient structure.

Figure 4:
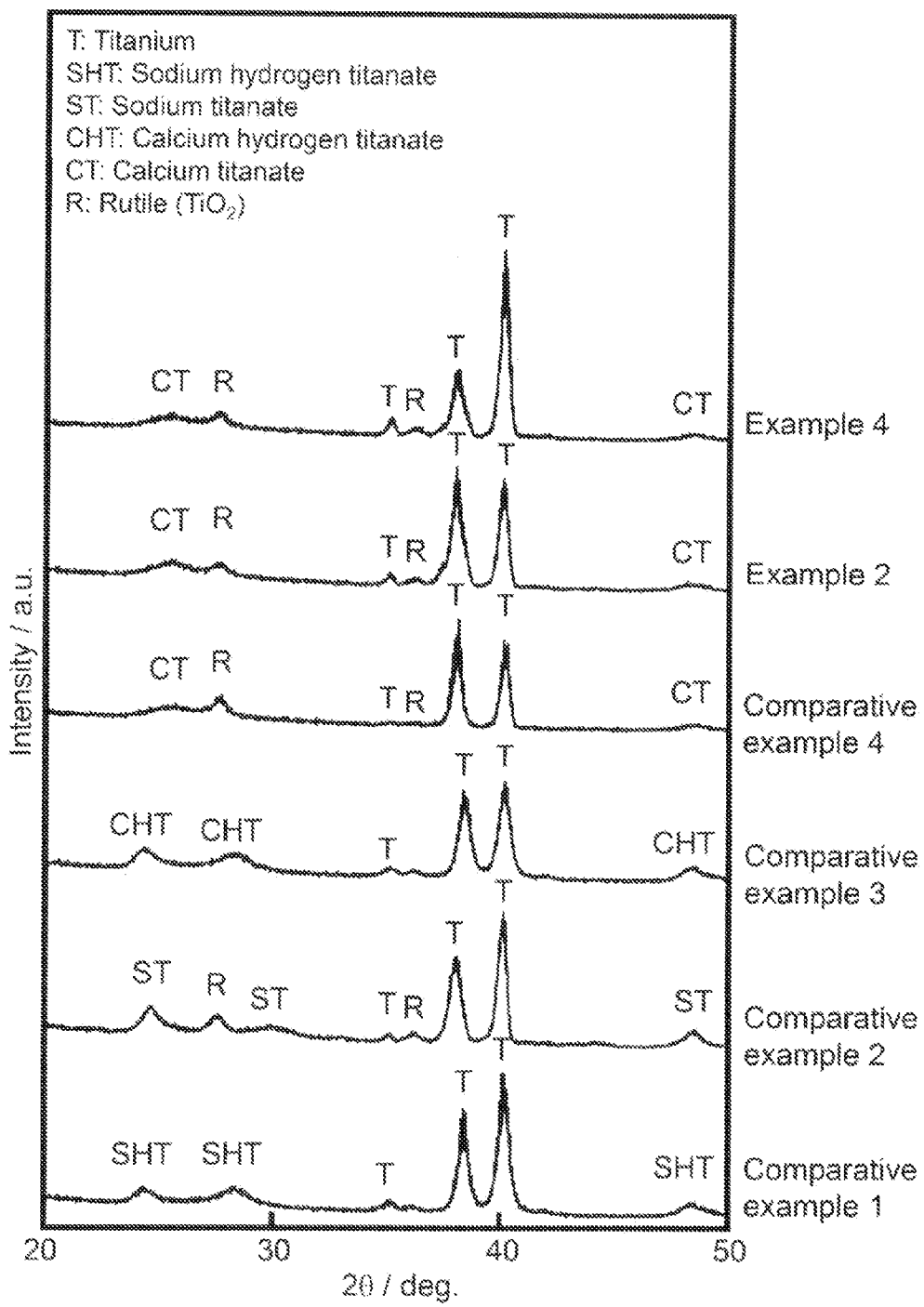
FIG. 4 is a graph that shows a thin film X-ray diffraction pattern of the surface of each titanium metal having been subjected to each treatment.

When the crystal structure of the surface of each specimen was examined by thin film X-ray diffractometry, it was shown that sodium hydrogen titanate was formed on the titanium metal surface after an alkali treatment (Comparative Example 1), calcium hydrogen titanate was formed after a calcium treatment (Comparative Example 3), and calcium titanate was formed after a heat treatment (Comparative Example 4) as shown in FIG. 4. No major change was observed in the structure even when a hot water treatment (Example 2) was performed.

The invention claimed is:

1. A method for producing a bone repair material, the method comprising:
    immersing a substrate made of titanium or a titanium alloy in a first aqueous solution that is free from calcium ions but contains at least one cation selected from the group consisting of sodium ions and potassium ions and is alkaline, then immersing the substrate in a second aqueous solution that is free from phosphate ions but contains calcium ions, then heating the substrate in a dry atmosphere, and then treating the substrate with hot water of 60° C. or higher or with steam.

2. The method of claim 1, wherein the first aqueous solution has an alkali concentration from 0.1 to 20 M and a temperature from 5 to 99° C., and the immersion time in the first aqueous solution is from 0.5 to 48 hours.

3. The method of claim 1, wherein the second aqueous solution contains at least one anion selected from the group consisting of chloride ion, nitrate ion, acetate ion and hydroxide ion.

4. The method of claim 1, wherein the second aqueous solution has a calcium concentration from 0.1 to 1,000 mM and a temperature from 5 to 99° C., and the immersion time in the second aqueous solution is from 0.5 to 48 hours.

5. The method of claim 1, wherein the heating temperature is from 400 to 800° C. and the heating time is from 0.5 to 24 hours.

6. The method of claim 1, wherein the treatment time with the hot water or steam is from 0.1 to 48 hours.

7. The method of claim 1, wherein the substrate is an alloy composed of Zr 3 to 15 in mass %, Nb 4 to 36 in mass %, Ta 2-13 in mass %, Ti above 53 in mass % and unavoidable impurities.

8. The method of claim 1, wherein said substrate includes at least one alloy selected from the group consisting of Ti-6Al-4V alloy, Ti-15Mo-5Zr-3Al alloy and Ti-6Al-2Nb-1Ta alloy.

* * * * *